United States Patent [19]

Ambrus et al.

[11] Patent Number: 5,112,815
[45] Date of Patent: May 12, 1992

[54] NOVEL 9 PH-DROXY-3-OXO-4, 24 (25)-STIGMASTADIEN-26-OIC ACID DERIVATIVES, A PROCESS FOR PREPARING SAME AND PHARMACEUTICAL COMPOSITIONS CONTAINING SAME

[75] Inventors: Gábor Ambrus; Andrea Maderspach; Antalné Jekkel; András Jávor; Éva Ilkoy; György Hajós; László Szporny, all of Budapest; József Nagy, Debrecen; Gyula Horváth, Budapest; Imre Moravcsik, Budapest, all of Hungary

[73] Assignee: Richer Gedeon Vegyeszet, Budapest, Hungary

[21] Appl. No.: 635,623
[22] PCT Filed: May 10, 1990
[86] PCT No.: PCT/HU90/00033
 § 371 Date: Feb. 17, 1991
 § 102(e) Date: Feb. 17, 1991
[87] PCT Pub. No.: WO90/13559
 PCT Pub. Date: Nov. 15, 1990

[30] Foreign Application Priority Data

May 11, 1989 [HU] Hungary ................ 2359/89

[51] Int. Cl.$^5$ .............. C07J 51/00; A61K 31/56
[52] U.S. Cl. ...................... 514/178; 552/540
[58] Field of Search ............... 514/178; 552/540, 544

[56] References Cited

U.S. PATENT DOCUMENTS 4,062,880 12/1977 Antosz et al. ............... 552/553

Primary Examiner—Marianne Cintins
Assistant Examiner—R. Cook
Attorney, Agent, or Firm—Keil & Weinkauf

[57] ABSTRACT

The invention relates to novel 9α-hydroxy-3-oxo-4,24(25)-stigmastadien-26-oic acid derivatives of the formula (I),

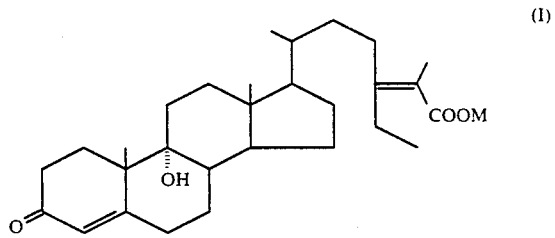

wherein M stands for hydrogen, $C_{1-4}$ alkyl or a pharmaceutically accteptable cation to a process for repairing these compounds and to compositions containing said compounds which exert an anti-hypercholesteremic effect.

6 Claims, No Drawings

NOVEL 9 PH-DROXY-3-OXO-4, 24 (25)-STIGMASTADIEN-26-OIC ACID DERIVATIVES, A PROCESS FOR PREPARING SAME AND PHARMACEUTICAL COMPOSITIONS CONTAINING SAME

This invention relates to novel 9α-hydroxy-3-oxo-4,24(25)-stigmastadien-26-oic acid derivatives of the formula (I),

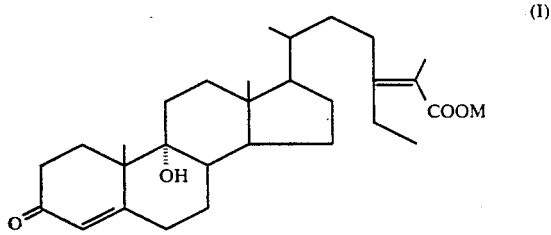

(I)

wherein M stands for hydrogen $C_{1-4}$ alkyl or a pharmaceutically acceptable cation, as well as pharmaceutical compositions containing these compounds.

The invention also relates to processes for preparing the compounds of the formula (I) by a microbial degradation of β-sitosterol or β-sitosterol-containing sterols of plant origin followed, if desired, by salt formation or esterification, and for preparing pharmaceutical compositions containing the compounds of the formula (I).

The pharmaceutically acceptable salts of the compounds of the formula (I) include those formed with inorganic or organic cations such as sodium, potassium, calcium, magnesium, aluminium, zinc, ammonium, ethylenediaminium, tris(hydroxymethyl)-aminomethane or tetramethylammonium.

The compounds of the formula (I) of this invention, wherein M is as defined above, are new and possess valuable pharmacological properties. They also serve as starting materials for preparing pharmaceutically important steroid derivatives.

It is known that bacteria using sterols as carbon source degrade both the steroid skeleton and the side-chain. The mechanism of the degradation of the side-chains of sterols was elucidated by C. J. Sih and co-workers [J. Am. Chem. Soc. 89, 1957 (1967); ibid. 104, 4718 (1982); ibid 104, 4720 (1982)]. The degradation of the side-chain of cholesterol begins with hydroxylation at the end of the side-chain. The oxidation of the hydroxyl group on the carbon atom in position 26 leads to the formation of a carboxylic acid which is degraded by the β-oxidation mechanism characteristic of fatty acids, resulting in a gradual shortening of the side-chain. The degradation of the side-chain of β-sitosterol having an ethyl group on the carbon atom in position 24 differs from that of cholesterol in that the bacteria degrading the side-chain introduce a carboxyl group on the carbon atom in position 28 attached to the carbon atom in position 24, then cleave the bond between the carbon atoms in positions 24 and 28 by a β-oxidation mechanism.

The enzymatic transformations affecting the steroid skeleton, which run parallel with the degradation of the side-chain, lead to the cleavage of the skeleton followed by a complete degradation of the ring system. The cleavage happens in such a way that steroid derivatives with the structure of 9 α-hydroxy-1,4-dien-3-one are formed from the sterols followed by a spontaneous rearrangement to yield therapeutically worthless seco-steroids in which the bond between the carbon atoms in positions 9 and 10 in ring B of the skeleton is cleaved [R. M. Dodson and R. D. Muir: J. Am. Chem. Soc. 83, 4627 (1961); K. Schubert and co-workers: Z. Naturforsch. 15b, 584 (1960)].

In the 1970s strains with changed genetic properties were prepared from sterol-utilizing bacteria by mutagenic treatments. These strains, having no active enzymes to catalyze the reactions initiating the degradation of the steroid skeleton.

It has also known that the cell wall of bacteria can be completely or partially removed by enzymatic hydrolysis under iso-osmotic conditions when protoplasts [J. Tomcsik and S. Guex-Holzer: Schweiz. Z. Allg. Path. Bact. 15, 517 (1952); C. Weibull: J. Bacteriol. 66, 688 (1953)] or spheroplasts [H. Sato and co-workers: Canad. J. Microbiol. 11, 807 (1965)] are formed the cell wall of which can be regenerated. The polyethylene-glycol-induced fusion of protoplasts or spheroplasts involves events of genetic recombination resulting in cells with new genetic information [K. Fodor and L. Alföldi: Proc. Natl. Acad. Sci. USA 73, 2147 (1976); P. Schaeffer and co-workers: Proc. Natl. Acad. Sci. USA 73, 2151 (1976); N. Rastogi and co-workers: J. Gen. Microbiol. 129, 1227 (1983); ibid. 137a, 135 (1986)].

Using the method of G. E. Peterson and co-workers [J. Lipid Reasearch 3, 275 (1962)] we isolated sitosterol-degrading microorganisms from various soil samples. Of the microorganism strains utilizing sterols we selected a Mycobacterium strain from which, by a mutagenic treatment using UV irradiation, we produced a mutant strain that no longer degrades the steroid skeleton.

By mutagenic treatment using N-methyl-N'-nitro-N-nitrosoguanidine we developed from this strain genetically labelled mutant strains, such as those requiring various nutrients (adenine, proline, valine) or those resistant to various antibiotics (e.g. streptomycin). By an in vivo genetic recombination using spheroplast fusion with these genetically labelled mutant strains we developed recombinant mycobacterium strains that partially degrade the sterol side-chain. Under the code name BCS 394 a Mycobacterium strain of this type producing new and unpublished sitosterol degradation products as main products such as 9 α-hydroxy-3-oxo-4,24(25)-stigmastadien-26-oic acid (I, wherein M stands for hydrogen) and 9 α-hydroxy-3-oxo-4,24(25)-stigmastadien-26-oic acid-methylester (I, wherein M means a methyl group) was deposited with the National Collection of Agricultural and Industrial Microorganisms (Budapest) under the number NCAIM B(P) 001038.

The taxonomic characteristics of the Mycobacterium strain deposited under the number NCAIM B(P) 001038 are as follows: the colonies of the microorganism are greyish white; this organism proliferates at 45° C., but fails to proliferate at 50° C. and in the absence of oxygen. It efficiently utilizes ammonium chloride, calcium nitrate, sodium nitrate and ammonium hydrogen phosphate as sole nitrogen source, as well as glucose glycerol, fructose, maltose, xylose, sodium succinate, sodium pyruvate and sodium acetate as sole carbon source. It fails to utilize saccharose, starch and arabinose. The stain is unable to degrade tryosine and is devoid of pigmentation.

We further found unexpectedly that the new compounds of the formula (I), wherein M has the same meaning as above, are potent inhibitors of the biosynthesis of cholesterol in mammals and efficiently reduce serum cholesterol levels.

In the 1980s epidemiologic studies revealed the fact that elevated serum cholesterol levels are a major risk factor in the development of atherosclerosis in coronary arteries. The main organ of cholesterol biosynthesis is the liver. The starting material for the synthesis is acetic acid and synthesis route to cholesterol includes mevalonic acid and squalene with a terpene structure as intermediates [K. Block: Angew. Chem. 77, 944 (1965); F. Lynen: Angew. Chem. 77, 929 (1965)].

Among substances inhibiting cholesterol biosynthesis a major importance has been attributed to 8(14)-dehydro-15-oxosterol derivatives, of which the most effective agent is 3β-hydroxy-5α-cholest-8(14)-en-15-one (Colestolone) whose significant serum cholesterol-lowering effect has been proved in several animal species and also in humans [G. J. Schroepfer jr. and co-workers: J. Biol. Chem. 263, 4110 (1988); G. J. Schroepfer Jr. and co-workers: Proc. Natl. Acad. Sci. USA 79, 3042 (1982)].

The cholesterol-biosynthesis-inhibiting effect of the compounds according to the invention is illustrated by the example of 9 α-hydroxy-3-oxo-4,24(25)-stigmastadien-26-oic acid (I, wherein M stands for hydrogen). The inhibitory effect of this compound was compared with that of 3β-hydroxy-5α-cholest-8(14)-en-15-one (Colestolone) by the method of A. Endo and co-workers [Eur. J. Biochem. 77, 31 (1977); Biochem. Biophys. Acta 486, 71 (1977)] studying in rat liver homogenate the incorporation of radiolabelled acetic acid into cholesterol.

Hannover Wistar male rats weighing 50–60 g were used for the experiment. Before the experiments the animals were fed for a week with rat chew enriched with 5% cholestyramine, in a reversed light cycle (light from 4 p.m. to 4 a.m., and dark from 4 a.m. to 4 p.m.). The food and water were available ad libitum.

The animals were decapitated on the day of the experiment, Livers were immersed in ice cold Krebs/Ringer bicarbonate buffer (pH 7.4) and cut into small pieces. Using a tissue homogenizer in a gentle mode of operation we prepared a crude liver homogenate of which a portion equivalent to 100 mg of wet liver was weighed into glass-stoppered tubes. The operations were carried out under constant cooling. The incubation mixture included the liver homogenate, the Krebs/Ringer bicarbonate buffer, the sodium-(1-$^{14}$C)acetate (supplied by IZINTA; specific activity: 14.86 MBq/mg) and the ($^{3}$H)cholesterol oleate (supplied by Du Pont; specific activity: 3067 GBq/mmole). The steroids inhibiting cholesterol biosynthesis were added to the incubation mixture in an alcoholic solution containing albumin, as described by G. J. Schroepfer and co-workers [J. Biol. Chem. 24, 8975 (1977)]. The final volume of the incubation mixture was 2.0 ml. Incubation went on for 2 hours in a water bath of 37° C., then 2 ml of alcohol containing 15% (w/v) of KOH were added to the mixture, which was then kept at 70°–75° C. for further 2 hours. The lipids were extracted from the alkaline mixture by petroleum ether. After evaporation of the solvent in nitrogen stream the dry residue was dissolved in a mixture of acetone and ethanol, then the cholesterol was precipitated by a solution of digitonin. The precipitate was centrifuged and dissolved in scintillation cocktail. The activity was measured for 5 minutes using a Hitachi scintillation spectrometer. The results obtained are presented in Table I.

TABLE I

| Compound | Concentration. μM | Inhibition. % |
|---|---|---|
| 3β-Hydroxy-5α-cholest-8(14)-en-15-one (reference) | 2.5 | 16.6 |
| | 10.0 | 55.0 |
| 9α-Hydroxy-3-oxo-4,24(25)-stigmastadien-26-oic acid | 2.5 | 65.3 |
| | 10.0 | 86.3 |

The data in Table I show that the cholesterol-biosynthesis-inhibiting effect of the compound according to the invention significantly surpasses the inhibiting effect of the known compound 3β-hydroxy-5α-cholest-8(14)-en-15-one (Colestolone) in a rat liver homogenate test.

In another aspect this invention relates to a process for producing new 9 α-hydroxy-3-oxo-4,24(25)-stigmastadien-26-oic acid derivatives of the formula (I), wherein M stands for hydrogen, $C_{1-4}$ alkyl or a pharmaceutically acceptable cation, by submerged aerobic fermentation of a Mycobacterium sp. BCS-394 microorganism strain, deposited under the number NCAIM B(P) 001038, or a mutants of same with β-sitosterol or a sterol mixture of plant origin containing β-sitosterol in a nutrient medium containing utilizable carbon and nitrogen sources as well as mineral salts, and, if desired, by isolating from the fermentation broth the compound or compounds of the formula (I), wherein M means hydrogen and/or a methyl group, and, if desired, by transforming the compound of the formula (I), wherein M stands for hydrogen, to a compound of the formula (I), wherein M stands for a pharmaceutically acceptable cation or $C_{1-4}$ alkyl group.

According to a preferred embodiment of the present invention the Mycobacterium strain BCS-394 deposited under the number NCAIM B(P) 001038 is cultivated in nutrient media which contain utilizable carbon and nitrogen sources as well as mineral salts, and which are suitable for the cultivation of fast-growing Mycobacteria.

Of the carbon sources glucose and glycerol, of the organic nitrogen sources soybean-meal, urea and yeast extract, of the inorganic nitrogen sources ammonium chloride were advantageously applied. It is advantageous to admix the sterol to be transformed in the form of a suspension prepared with Tween-80 and polypropylene-glycol with the nutrient medium. Pure β-sitosterol or a sterol mixture containing β-sitosterol, e.g. crude sitosterol obtained from soybean oil, which is a mixture of β-sitosterol and campesterol, serve as substrates for the microbial transformation.

The cultivation of the microorganisms and the transformation of the sterols are carried out between 28° C. and 37° C., preferably at 32° C.

A major proportion of the products of sterol transformation is absorbed on the mycobacterium cells, a minor proportion is dissolved in the nutrient liquid. The steroids are desorbed from the cells using organic solvents miscible with water, preferably methanol, while the sterol transformation products in the filtrate of the fermentation broth are preferably isolated by extraction with ethyl acetate or chlorinated hydrocarbons, such as dichloromethane. In addition to the main products 9α-hydroxy-3-oxo-4,24(25)-stigmastadien-26-carboxylic acid and its methyl ester, the crude product obtained after the evaporation of the solvent also contains several sterol degradation products present in minor quantities. For the separation of the sterol transformation products column chromatography and/or thin-layer chromatography can be preferably used. The structures of the products were elucidated by UV, IR, $^1$H-NMR and $^{13}$C-NMR as well as mass spectrometry.

From the compounds prepared by the process according to this invention and having the formula (I), wherein M means hydrogen, salts can be formed for therapeutic application. These salts can be prepared in a manner known per se from the compound of the formula (I), wherein M stands for hydrogen, and a base providing the suitable cation.

The ester derivatives according to the invention can be prepared also in a manner known per se from the compound of the formula (I), wherein M means hydrogen, and a suitable $C_{1-4}$ alcohol. However, a representative of the compounds according to the invention, wherein M means a methyl group in the formula (I), can be isolated directly from the fermentation broth.

The compounds of the formula (I) according to the invention, wherein M stands for hydrogen, $C_{1-4}$ alkyl group or a pharmaceutically acceptable cation, are highly useful as active substances in antihypercholestermic pharmaceutical compositions for the treatment of e.g. atherosclerosis or hyperlipemia in humans. They can be administered e.g. orally or parenterally, in the form of e.g. tablets, capsules or injectable compositions. The oral mode of administration is generally preferred. The dose may naturally depend on several factors, such as the age, body weight, the severity of the health problem of the person to be treated and on some other factors, but the daily dose for adults may generally range between about 100 and 3000 mg, preferably between 300 and 1000 mg, but higher doses may also be favourably used, if necessary.

For therapeutic applications, the active compounds according to the invention are suitably transformed to pharmaceutical compositions by mixing them with non-toxic, inert, solid or liquid carriers and/or additives commonly used for enteral or parenteral administration.

According to the invention, solid forms of pharmaceutical compositions suitable for oral administration can be prepared from 9α-hydroxy-3-oxo-4,24(25)-stigmastadien-26-oic acid derivatives of the formula (I), wherein M has the above meaning, by the following method:

The pulverized active substance with an average particle size of 0.05-1.0 mm is homogenized with additives of similar particle size, used in preparing tablets and capsules, then the mixture is filtered in hard gelatine capsules or pressed to form tablets directly or after dry or wet granulation.

Vehicles used in the preparation of tablets and capsules were applied as additives, preferably starch, tribasic calcium phosphate, calcium hydrogen phosphate, lactose, glucose, cellulose, saccharose, mannitol, sorbitol or mixtures thereof; adsorbents, preferably colloidal silicon dioxide (protected names: Aerosil, Gesilite, Cab-o-sil, Syloid, Neosyl); excipients, preferably gelatine, acacia, cellulose ethers (methylcellulose, carboxymethylcellulose, ethylcellulose, ethyl-hydroxyethylcellulose, hydroxypropyl-methylcellulose), pectin, sodium alginate, tragacanth, polyvinylpyrrolidone, polyvinylalcohol or their mixtures; disintegrants, preferably starch, sodium carboxymethyl-starch, ultra-amylopectin, alginic acid and alginates, formaldehyde-gelatine, formaldehyde-casein, pectin, bentonite, microcrystalline cellulose or mixtures thereof; glidants, lubricants and antiadhesive materials (preferably metal soaps, magnesium and calcium stearate), glycerol monostearate, stearylalcohol, cetylalcohol, polyethylene glycol, talc or their mixtures.

The invention is illustrated in detail by the following Examples.

EXAMPLE 1

Preparation of 9α-hydroxy-3-oxo-4,24(25)-stigmastadien-26-oic acid and methylester thereof A cell suspension is prepared with 10 ml of sterile water from the 5-day old culture of Mycobacterium sp. BCS-394 (NCAIM B(P) 001038) grown on a potato-glucose agar slant. Five ml of this suspension are used to inoculate 800 ml of sterile MI inoculum-medium in a 3000 ml Erlenmeyer flask. The MI medium has the following composition:

| Glucose | 8.0 g |
|---|---|
| Soybeanmeal | 1.6 g |
| Urea | 0.4 g |
| Yeast extract | 0.8 g |
| Ammonium chloride | 2.4 g |
| Potassium dihydrogen phosphate | 0.4 g |
| Magnesium sulfate.7H$_2$O | 0.4 g |
| Ferric chloride.6H$_2$O | 0.4 g |
| Tween-80 | 0.4 g |
| in 800 ml of tap water. | |

The pH of the nutritive medium is adjusted to 7.0 before sterilization and the mixture is sterilized at 121° C. for 45 minutes.

The flask is incubated at 32° C. for 2 days on a rotary shaker (250 r.p.m., diameter 2.5 cm). The contents of this flask are used to inoculate, in a 10 l laboratory fermentor, 4.2 l of MF medium, sterilized at 121° C. for 60 minutes.

The MF medium is prepared as follows:

50 g of glucose, 10 g of soybean-meal, 2.5 g of urea, 15 g of ammonium chloride and 2.5 g of potassium dihydrogen phosphate are brought to boil in 1.5 l of tap water. The basic medium prepared in this way is added, supplemented with 15 g of calcium carbonate, under constant stirring to the molten mixture of 100 g of β-sitosterol, 40 g of polypropylene glycol, 10 g of Tween-80 and 800 ml of tap water, sterilized at 121° C. for 1 hour, then the volume of the mixture is brought up to 4 l with boiling tap water. The nutrient medium thus obtained is sterilized at 121° C. for 1 hour.

The inoculated culture is agitated at 32° C. for 24 hours at 750 r.p.m., while an air flow of 100 l/hour is introduced to the fermentor. Fermentation is continued for 6 days with aeration of 300 l/hour through the broth stirred at 750 r.p.m. After the termination of the fermentation the products of the sterol transformation are isolated as follows.

The cells of 1 l of the broth, which initially contained 20 g of β-sitosterol, are filtered, then the adhering sterol conversion products and the unchanged β-sitosterol are washed off three times with 200 ml of methanol. The filtrate of the broth is extracted with 200 ml of ethyl acetate.

After the evaporation of the pooled methanol and ethyl acetate extracts under reduced pressure 22 g of raw product are obtained which are subjected to chromatography on a column prepared from 400 g of silicic acid. Elution is carried out with the ethyl acetate-n-heptane in which the proportion of ethyl acetate is increased step-wise. Fractions eluted with an ethyl acetate-n-heptane mixture containing 10% of ethyl acetate are evaporated. After recrystallizing the residue from methanol 0.15 g of 4-stigmastadien-3-one is obtained. m.p. 89° to 90° C.

UV spectrum (in ethanol): $\lambda_{max}$ 243 nm ($\epsilon = 14090$);

iR spectrum (in KBr): $\nu C=O$ 1678, $\nu C=C$ 1616 cm$^{-1}$;

1H-NMR spectrum (in CDCl$_3$, $\delta$): 5.56 s (H-4), 1.16 s (3 H-19), 0.68 s (3 H-18) ppm;

Mass spectrum: molecule-ion (m/z): 412;

Characteristic ions (m/z): 412, 229, 135, 124, 109, 95, 55, 43.

Using a solvent mixture containing 20% of ethyl acetate in n-heptane 1.05 g of unchanged β-sitosterol are eluted from the column.

Fractions eluted with an eluent mixture containing 30% of ethyl acetate in n-heptane are evaporated under reduced pressure. After recrystallizing the residue from methanol 1.8 g of 9 α-hydroxy-3-oxo-4,24(25)-stigmastadien-26-oic acid methyl ester are obtained, m.p. 187° to 189° C.

UV spectrum (in ethanol): $\lambda_{max}$ 239 nm ($\epsilon = 21530$);

IR spectrum (in KBr): $\nu$OH 3600–3400, $\nu_{max}$ 3487 (9α-hydroxyl group), $\nu C=O$ 1717 (conjugated ester), 1678 (ketone in position 3), $\nu C=C$ 1615 cm$^{-1}$;

1H-NMR spectrum (in C$_6$O$_6$, $\delta$): 5.92 s (H-4), 3.46 s (3 H, OCH$_3$), 2.58 q (2 H-28), 1.96 s (3 H-27), 1.22 t (3 H-29), 0.95 d (3 H-21), 0.8 s (3 H-19), 0.55 s (3 H-18) ppm.

Mass spectrum: molecule-ion (m/z): 470;

Characteristic ions (m/z): 470, 438, 410, 137, 136, 134,

Fractions eluted with an eluent mixture containing 35% of ethyl acetate in n-heptane are evaporated under reduced pressure. After recrystallizing the residue from methanol 0.15 g of 9α-hydroxy-27-nor-4-cholestene-3,24-dione is obtained, m.p. 208° to 211° C.

UV spectrum (in ethanol): $\lambda_{max}$ 241 nm ($\epsilon = 14800$);

IR spectrum (in KBr): $\nu$OH 3555, $\nu C=O$ 1705 (ketone in position 24), 1660 (ketone in position 3), $\nu C=C$ 1614 cm$^{-1}$;

1H-NMR spectrum (in CDCl$_3$, $\delta$): 5.86 s (H-4), 1.32 s (3 H-19), 1.05 t (3 H-26), 0.90 d (3 H-21), 0.72 s (3 H-18) ppm;

Mass spectrum: molecule-ion (m/z): 400;

Characteristic ions (m/z): 400, 151, 137, 136, 124, 122, 109, 57.

Fractions eluted with an eluent mixture containing 40% of ethyl acetate in n-heptane are evaporated. After recrystallizing the residue from acetone 0.2 g 9α-hydroxy-3-oxo-23,24-dinor-4-cholen-22-oic acid methyl ester is obtained, m.p. 212° to 216° C.

UV spectrum (in ethanol): $\lambda_{max}$ 242 nm ($\epsilon = 15860$);

IR spectrum (in KBr): $\nu$OH 3395, $\nu C=O$ 1730 (ester), 1650 (ketone in position 3), $\nu C=C$ 1615 cm$^{-1}$;

1H-NMR spectrum (in CDCl$_3$, $\delta$): 5.8 s (H-4), 3.6 s (OCH$_3$), 1.3 s (3 H-19), 1.2 d (3 H-21), 0.7 s (3 H-18) ppm;

Mass spectrum: molecular-ion (m/z): 374;

Characteristic ions (m/z): 374, 180, 151, 137, 136, 124, 109, 81.

Fractions eluted with an eluent mixture containing 42% of ethyl acetate in n-heptane are evaporated. After recrystallizing the residue from methanol 0.25 g of 3-oxo-4-stigmastadien-26-oic acid is obtained, m.p. 164° to 168° C.

UV spectrum (in ethanol): $\lambda_{max}$ 242 nm ($\epsilon = 14010$);

IR spectrum (in KBr): $\nu C=O$ 1736, 1650 (the carboxylic acid in position 26 and the oxo group in position 3); $\nu C=C$ 1616 cm$^{-1}$;

1H-NMR spectrum (in CDCl$_3$, $\delta$): 5.73 s (H-4), 1.19 s (3 H-19), 0.7 s (3 H-18) ppm;

Mass spectrum: molecule-ion (m/z): 442;

Characteristic ions (m/z): 442, 424, 229, 147, 124, 123, 95, 55.

Fractions eluted with an ethyl acetate-n-heptane mixture containing 45% of ethyl acetate are evaporated under reduced pressure. The 2.5 g of residue thus obtained are dissolved in 10 ml of methanol to which 10 ml of a mixture containing 10% (w/v) of hydrochloric acid in methanol, and 50 ml of ethyl acetate are added. The solution thus obtained is washed twice with 30 ml of distilled water and then evaporated under reduced pressure. After recrystallizing the residue from methanol 2.2 g of 9α-hydroxy-3-oxo-4,24(25)-stigmastadien-26-oic acid are obtained, m.p. 242° to 248° C.

UV spectrum (in ethanol): $\lambda_{max}$ 239 ($\epsilon = 21230$);

IR spectrum (in KBr): $\nu$OH 3650–3350, $\nu_{max}$ 3483 (9α-hydroxy group), 3200–2000 (carboxylic acid in position 26), $\nu C=O$ 1676 (ketone in position 3 and carboxylic acid in position 26), $\nu C=C$ 1616 cm$^{-1}$;

1H-NMR spectrum (in C$_5$D$_5$N, $\delta$): 6.15 d (H-4), 2.83 q (2H-28), 2.28 s (3 H-27), 1.39 s (3 H-19), 1.39 t (3 H-29), 1.14 d (3 H-21), 0.89 s (3 H-18) ppm;

Mass spectrum: molecule-ion (m/z): 4.56;

Characteristic ions (m/z): 456, 438, 410, 137, 136, 124, 123, 110.

EXAMPLE 2

Preparation of 9α-hydroxy-3-oxo-4,24(25)-stigmastadien-26-oic acid and methyl ester thereof A cell suspension is prepared with 10 ml of sterile water from the 4–5 day old culture of Mycobacterium sp. BCS-394 grown on a potato-glucose agar slant. Ten 100 ml portions each of sterile MY-5 inoculum-medium in ten 500 ml Erlenmeyer flasks are inoculated with 1 ml each of the above cell suspension.

The MY-5 medium is prepared as follows:

10 g of glycerol, 1 g of soybeanmeal, 0.5 g of urea, 1 g of ammonium chloride, 0.5 g of dipotassium hydrogen phosphate, 0.5 g of magnesium sulfate .7H$_2$O, 1 g of sodium citrate and 0.05 g of ferric chloride .6H$_2$O are brought to boil in 300 ml of tap water. The basis medium prepared in this way is added, under stirring, to the molten mixture of 30 g of crude sitosterol (a 2:1 mixture of β-sitosterol and campesterol), 8 g of polypropyleneglycol, 2 g of Tween-80 and 150 ml of tap water, sterilized at 121° C., then the volume of the mixture is brought up to 1 l with boiling tap water.

The flasks are shaken at 32° C. for 7 days on a horizontal shaker (250 r.p.m., diameter: 2.5 cm), then the cells are separated from the broth by means of a centrifuge. The sterol conversion products and the unchanged crude sitosterol are washed off from the cells by washing them three times with 200 ml of methanol each. The methanol solution is evaporated under reduced pressure. The supernatant of the fermentation broth is extracted with 200 ml of ethyl acetate and the extract is evaporated under reduced pressure. By pooling the residue of the extracts 32 g of crude product are obtained. The crude product is subjected to chromatography on a column prepared from 500 g of silicic acid. Elution is carried out with an ethyl acetate-n-heptane mixture in which the proportion of ethyl acetate is increased step-wise. Using an eluent mixture containing 25% of ethyl acetate in n-heptane 2.5 g of unchanged starting material (a 2:1 mixture of β-sitosterol and campesterol) are eluted from the column.

Fractions eluted with a mixture containing 30% of ethyl acetate in n-heptane are evaporated under reduced pressure. After recrystallizing the residue from methanol 3.4 g of 9 α-hydroxy-3-oxo-4,24(25)-stigmastadien-26-oic acid methyl ester are obtained, m.p. 187° to 189° C.

The spectral characteristics of the product are the same as those presented in Example 1.

Fractions eluted with a mixture containing 35% of ethyl acetate in n-heptane are evaporated under reduced pressure. After recrystallizing the residue from methanol 0.43 g of 9α-hydroxy-27-nor-4-cholesten-3,24-dione is obtained, m.p. 208° to 211° C.

The spectral characteristics of the product are the same as those presented in Example 1.

Fractions eluted with a mixture containing 37% of ethyl acetate in n-heptane are evaporated. After recrystallizing the residue from acetone 0.49 g of 9α-hydroxy-3-oxo-23,24-dinor-4-cholen-22oic acid methyl ester is obtained, m.p. 212° to 216° C.

The spectral characteristics of the product are the same as those presented in Example 1.

Fractions eluted with a mixture containing 40% of ethyl acetate in n-heptane are evaporated. After recrystallizing the residue from methanol 0.25 g of 9α-hydroxy-26,27-dinor-4-cholestene-3,24-dione is obtained, m.p. 201° to 204° C.

UV spectrum (in ethanol: $\lambda_{max}$ 241 nm, ($\epsilon$=14200);

IR spectrum (in KBr): $\nu$OH 3550, $\nu$C=O 1705 (ketone in position 24), 1660 (ketone in position 3), $\nu$C=C 1610 cm$^{-1}$;

$^1$H-NMR spectrum (in CDCl$_3$, δ): 5.85 s (H-4), 2.12 s (3 H-25), 1.3 s (3 H-19), 0.90 d (3 H-21), 0.7 s (3 H-18) ppm;

Mass spectrum: molecule-ion (m/z): 386;

Characteristic ions (m/z): 386, 151, 137, 136, 124, 109, 43.

Fractions eluted with a mixture containing 45% of ethyl acetate in n-heptane are evaporated under reduced pressure. The residue is purified using preparative thin layer chromatography with the following developing solvent: ethyl acetate and n-heptane in a ratio of 4 to 6. The 4 g product thus obtained are dissolved in 10 ml of methanol, the solution is acidified with 10 ml of 10% methanolic hydrochloric acid, then diluted with 50 ml of ethyl acetate. The solution obtained is washed twice with 30 ml of distilled water each and then evaporated under reduced pressure. After recrystallizing the residue from methanol 3.5 g of 9α-hydroxy-3-oxo-4,24-(25)-stigmastadien-26-oic acid are obtained, m.p. 242° to 248° C.

The spectral characteristics of the product are the same as those presented in Example 1.

EXAMPLE 2

Sodium salt of 9α-hydroxy-3-oxo-4,24(25)-stigmastadien-26-oic acid

To a solution of 100 mg of 9α-hydroxy-3-oxo-4,24(25)-stigmastadien-26-oic acid in 25 ml of ethanol 2.2 ml of 0.1N sodium hydroxyd are added. After standing for 30 minutes at room temperature the solution is evaporated in vacuo. The oily residue obtained is taken up in 10 ml of ethanol and the solution is evaporated. 5 ml of acetone are added to the residue and the resulting sodium salt of 9α-hydroxy-3-oxo-4,24(25)-stigmastadien-26-oic acid is filtered.

IR spectrum (in KBr): $\nu$OH 3495, $\nu$C=O 1660 (oxo group in position 3), $\nu$COO$^-$ 1572 cm$^{+1}$;

Mass spectrum with fast atom bombardment (FAB): [M+Na]$^-$=501.

What we claim is:

1. A 9α-hydroxy-3-oxo-4,24(25)-stigmastadien-26-oic acid derivative of the formula (I),

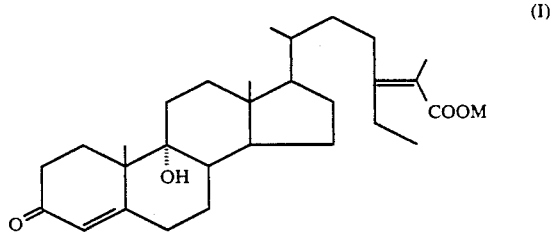

wherein M stands for hydrogen, C$_{1-4}$ alkyl or a pharmaceutically acceptable cation.

2. 9α-Hydroxy-3-oxo-4,24(25)-stigmastadien-26-oic acid.

3. A C$_{1-4}$ alkyl ester of 9α-hydroxy-3-oxo-4,24(25)-stigmastadien-26-oic acid.

4. 9α-Hydroxy-3-oxo-4,24(25)-stigmastadien-26-oic acid methyl ester.

5. A pharmaceutically acceptable salt of 9α-hydroxy-3-oxo-4,24(25)-stigmastadien-26-oic acid.

6. A pharmaceutical composition having a serum cholesterol-lowering effect which comprises as an active ingredient an effective amount of a 9α-hydroxy-3-oxo-4,24(25)-stigmastadien-26-oic acid derivative as defined in claim 1, in admixture with a pharmaceutically acceptable carrier.

* * * * *

UNITED STATES PATENT AND TRADEMARK OFFICE
CERTIFICATE OF CORRECTION

PATENT NO. : 5,112,815

DATED : May 12, 1992

INVENTOR(S) : AMBRUS, MADERSPACH, JEKKEL, JAVOR, ILKOY, HAJOS, SZPORNY, NAGY, HORVATH, MORACSVIK

It is certified that error appears in the above-identified patent and that said Letters Patent is hereby corrected as shown below:

in the Abstract, line 5, delete "accteptable" and insert therefor --acceptable--.

in the abstract, line 5, delete "repairing" and insert therefor --preparing--.

Signed and Sealed this

Thirteenth Day of July, 1993

Attest:

MICHAEL K. KIRK

Attesting Officer

Acting Commissioner of Patents and Trademarks